United States Patent [19]

Hawkins et al.

[11] 4,049,698
[45] Sept. 20, 1977

[54] PROCESS FOR PRODUCING METHYLENE MALONIC ESTERS

[75] Inventors: Gary Fred Hawkins; Robert Lee Gass, both of Kingsport, Tenn.

[73] Assignee: Eastman Kodak Company, Rochester, N.Y.

[21] Appl. No.: 711,924

[22] Filed: Aug. 5, 1976

[51] Int. Cl.² .................. C07C 69/74; C07C 67/30
[52] U.S. Cl. .................. 560/127; 260/257; 560/190; 560/201
[58] Field of Search .................. 260/485 R, 468 K

[56] References Cited

U.S. PATENT DOCUMENTS

| | | | |
|---|---|---|---|
| 2,212,506 | 8/1940 | Bachman et al. | 260/485 |
| 2,264,354 | 12/1941 | Adler et al. | 260/464 |

OTHER PUBLICATIONS

Chemical Abstracts 50 19430c (1955).
March, Advanced Organic Chemistry, p. 698, (1969).

Primary Examiner—Robert Gerstl
Attorney, Agent, or Firm—Elliott Stern; Daniel B. Reece, III

[57] ABSTRACT

A process comprising
  A. reacting an ester of malonic acid having the formula

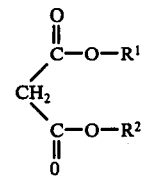

with formaldehyde and a diene having the formula

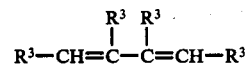

in the presence of an amine catalyst at about reflux temperature to form a compound having the formula

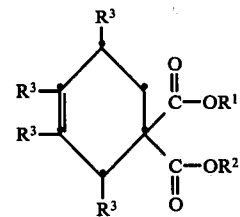

wherein $R^1$ and $R^2$ are the same or different and each represents alkyl of 1 to about 10 carbon atoms, cyclohexyl or alkenyl of 2 to about 4 carbon atoms and each $R^3$ is the same or different and represents hydrogen, methyl or ethyl.

8 Claims, No Drawings

PROCESS FOR PRODUCING METHYLENE MALONIC ESTERS

It is known to produce methylene malonic esters from the corresponding malonic ester and para-formaldehyde in accordance with the following reaction equation:

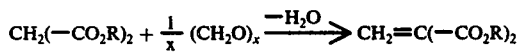

where R is a branched or unbranched aliphatic residue with 1 to 4 carbon atoms. (J. Chem. Soc. Japan, Inc. Chem. Sect. 56, 901–903 (1953), c.a. 49, p. 1780g, and U.S. Pat. No. 3,758,550.)

It is also known that the monomeric esters of malonic acid may be prepared by hydrogenating the olefinic bond of a dialkyl alkoxy methylene malonate and pyrolyzing the reaction product. See, for example, U.S. Pat. No. 3,523,097. We have now discovered a process for producing intermediates which may be used to produce methylene malonic esters which comprises reacting an ester of malonic acid having the formula

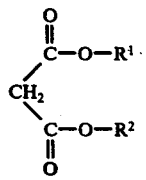

with formaldehyde and a diene having the formula

in the presence of a primary, secondary or tertiary amine, at about refllux temperature to form a compound having the formula

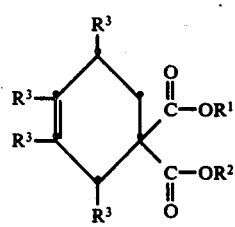

wherein
R$^1$ and R$^2$ are the same or different and each represents alkyl of 1 to about 10 carbon atoms, cyclohexyl or alkenyl of 2 to about 4 carbon atoms and each R$^3$ is the same or different and represents hydrogen, methyl or ethyl.

The compounds thus produced are readily converted by pyrolyzation at temperature in excess of 600° C. to dialkyl methylene malonates having the formula:

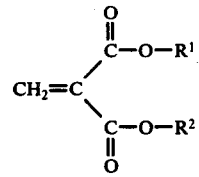

wherein
R$^1$ and R$^2$ are as defined above.

Examples of the groups representative of R$^1$ and R$^2$ are methyl, ethyl, propyl, butyl, hexyl, decyl, methallyl, alkyl, 1-propenyl, 2-propenyl, n-butynyl, etc.

The reaction of this invention is carried out in the presence of a catalyst selected from primary, secondary and tertiary amines, the preferred ones (giving higher yields) being a secondary aliphatic amine. The salts of these amines with organic monocarboxylic acids, such as piperidine acetate, also act as effective catalysts.

The preferred catalysts are secondary amines such as piperidine, piperazine, N-methylpiperazine, dibutylamine, morpholine, diethylamine and the like.

Other catalyst that perform less well are pyridine, triethylamine, tripropylamine, triethylenediamine, N,N-dimethylpiperazine, butylamine, pentylamine, hexylamine, heptylamine, nonylamine, decylamine and the like. The reaction is generally carried out using an excess of diene at about reflux temperature, e.g., about 50° C. to about 110°C. (preferably 70° C. to about 90° C.) to form an adduct mixture and water, azeotroping out the latter with the excess diene. The other reactants are generally combined in about equimolar amounts. As used herein the term "formaldehyde" relates to any source of the compound having the formula

such as paraformaldehyde, formalin, gaseous formaldehyde and the like. It has been discovered that the novel intermediates of this invention are produced in accordance with the following reaction equation:

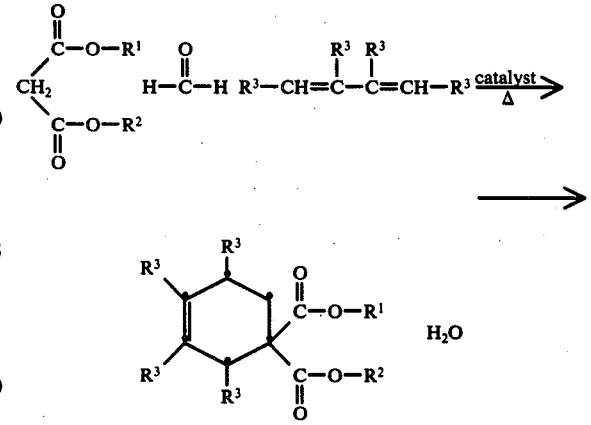

wherein
each R$^3$ is the same or different and is selected from hydrogen, methyl or ethyl.

Examples of dienes utilizable in the process of the invention are 2-methyl-1,3-pentadiene, 1,3-hexadiene, cyclopentadiene, isoprene, 1,3-butadiene, 2,4-hexadiene, 2,3dimethyl-1,3-butadiene, etc. The amount of catalyst utilized is generally in the range of 0.1 to about 5 weight percent based on the weight of the malonate ester.

The intermediates prepared by the process of this invention are not only useful in preparing methylene malonate adhesives, but also barbiturates.

The compounds made by the method of our invention, when pyrolyzed, give higher yields and purer methylene malonates than the methods taught in the prior art. See, for example, U.S. Pat. Nos. 2,313,501 and 2,330,033 as well as Organic Syntheses, 38, 22–25.

The reaction is preferably carried out at atmospheric pressure, however, sub- or superatmosheric pressure may be utilized. While the reaction is preferably carried out in the presence of an inert atmosphere, it may be carried out in the presence of oxygen.

It is preferred that the pyrolysis of the product formed above be carried out in a steel pyrolysis tube without packing or packed with "protruded stainless steel" packing. Pyrolysis of 1,1-dicarbomethoxy-2,4-dimethyl-3-cyclohexene indicated that, with the materials used, temperatures in excess of 600° C. are required to give a high percentage of pyrolysis. Pyrolysis of these compounds at about 670° C. gave dimethyl methylene malonate of high quality (c.a. 100%) in 66.5% yield. This reaction proceeds according to the following reaction equation:

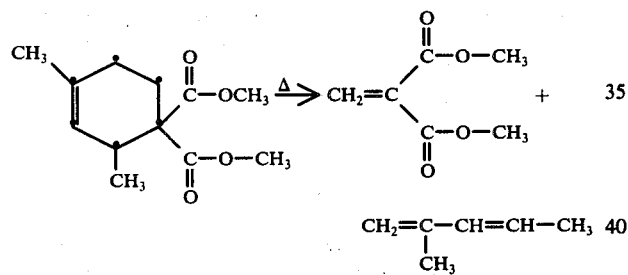

Generally, the pyrolysis step is carried out at subatmospheric pressure.

The following examples illustrate the invention.

DESCRIPTION OF PYROLYSIS APPARATUS

Heating Element — Blue M Stabil Glow, Combustion Tube Furnace, Model TF-2420 C-4, capable of heating to 1,000° C.

Combustion Tube — Stainless steel tube, 1 ¼ inches in outside diameter with a stainless steel ball joint on one end and an elbow and stainless steel ball joint on the other. One end of the tube is connected to a three-neck flask which is fitted with stirrer, thermometer, and heating mantle. The other end (with the elbow) is connected directly to a flask fitted with $SO_2$ gas inlet tube and a reflux condenser. The flask is cooled by a water bath, kept at such a temperature that desired product condenses but by-product diene does not. The upper end of the reflux condenser is connected to ¾ inch O.D. copper tubing, the other end of which is connected to a dry ice-acetone trap which is in turn connected to another trap and a vacuum pump. Typically a vacuum of about 0.2 mm. Hg can be obtained in the closed system unless decomposition is occurring.

EXAMPLE 1

1,1-Dicarbomethoxy 2,4-dimethyl 3-cyclohexene

A mixture of 264 g. (2.0 moles) of dimethyl malonate and 62 g. (2.06 moles) of paraformaldehyde was prepared and added in about 5 portions to 300 g. (3.7 moles) of 2-methyl-1,3-pentadiene, 1 ml. of piperidine and 50 ml. of pyridine, azeotroping out the water between additions. After 37 ml. of water (theory = 36 ml.) was collected and azeotroping had ceased, the reaction mixture was stripped, finally under house vacuum, to 125° C. to remove pyridine.

100 Milliliters of xylene was then added and stripping repeated finally under good vacuum (<0.1 mm. Hg) to about 110° C. pot temperature, to aid in the removal of pyridine and unreacted piperidine.

The product was finally distilled, coming over mostly at 90° C./0.1–0.3 mm. Hg. The product is a solid at moderate temperatures, requiring a change in the condensing system. The yield was 287.5 g., 62% of theory. By NMR the product is found to be practically pure 1,1-dicarbomethoxy-2,4-dimethyl-3-cyclohexene.

591 Grams of 1,1-dicarbomethoxy-2,4-dimethyl-3-cyclohexene was distilled through the pyrolysis tube at 670–675° C., under vacuum, beginning at about 2 mm. but gradually rising, possibly due to decomposition, to over 10 mm.

334.5 Grams of product was collected in the receiver containing polyphosphoric acid and hydroquinone; 234 g. was collected in the first trap and 14 g. in the pump trap. The residue from the distillation was 5 g.

After stirring the product at 35° C. for 15 minutes with the polyphosphoric acid, it was allowed to stand overnight and decanted. The organic layer was distilld giving 249 g. of product and 38 g. residue. The product assays essentially 100%. Yield is 66% of theory.

EXAMPLE 2

1-Carbomethoxy 1-carboalloxy 2,4(or 3,5)-dimethyl 3-cyclohexene

To a 1 liter flask equipped with stirrer, thermometer, dropping funnel and Dean-Stark tube with condenser, was added 328 g. (4.0 moles) of 2-methyl-1,3-pentadiene, 2 ml. of piperidine, and 10 ml. of pyridine.

A slurry of 63 grams (2.1 moles as formaldehyde) of paraformaldehyde in 316 g. (2.0 moles) of methyl allyl malonate was prepared. This slurry was added slowly to the stirred flask containing the 2- methyl-1,3-pentadiene, piperidine and pyridine while refluxing the 2-methyl-1,3-pentadiene to remove the water formed as an azeotrope.

When all of the slurry had been added and water had ceased to azeotrope, 36 ml. of water had been collected. 1 Gram of hydroquinone and 50 ml. of toluene are added and the low boiling materials stripped out at up to 112° C. with a vacuum of about 0.2 mm. Hg.

511 Milliliters of benzene and 25 g. of scavenger (the reaction product of 3 moles of methanol with 1 mole of phosphorus pentoxide) were added and the mixture refluxed for 10 minutes. The oily layer was allowed to settle to the bottom and the top layer was decanted into a still. The solution was distilled, the product boiling at about 87° C./0.1 mm. Hg. Yield = 339 g. (74.5% of theory). Residue = 98.5 g.

EXAMPLE 3

Repetition of Example 2, omitting the pyridine and using 3 ml. of piperidine gave product in 80% yield.

EXAMPLE 4

1,1-Dicarbomethoxy 2,4,6-trimethyl 3-cyclohexene AND 1,1-Dicarbomethoxy 2,4-dimethyl 6-propyl 3-cyclohexene Repetition of procedures similar to Example 3 substituting acetaldehyde in one experiment and butyraldehyde in the other for paraformaldehyde gave mixtures of products, less than 15% being the desired cyclic adduct.

EXAMPLE 5

Spiro-2',4'-dimethyl-3'-cyclohexene-1',5-barbituric acid

To a solution resulting from the reaction of 6.9 g. of sodium with butanol in 210 ml. of the latter was added 12 g. of urea and 22.6 g. of 1,1-dicarbomethoxy-2,4-dimethyl-3-cyclohexene. The mixture was stirred at about 92° C. for 6 hours, cooled to 25° C. and filtered to give 23 g. of the disodium salt of the desired product.

The disodium salt was treated with cold dilute hydrochloric acid to obtain the free barbituric acid derivative. The $C^{13}$ NMR spectrum indicates that the product was the expected one.

The invention has been described in detail with particular reference to certain preferred embodiments thereof, but it will be understood that variations and modifications can be effected within the spirit and scope of the invention.

We Claim:
1. A process comprising
   A. reacting an ester of malonic acid having the formula

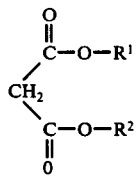

with formaldehyde and a diene having the formula

in the presence of a catalyst selected from primary, secondary and tertiary amines at about reflux temperature to form a compound having the formula

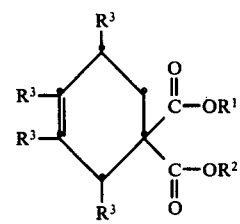

wherein $R^1$ and $R^2$ are the same or different and each represents alkyl of 1 to about 10 carbon atoms, cyclohexyl or alkenyl of 2 to about 4 carbon atoms and each $R^3$ is the same or different and represents hydrogen, methyl or ethyl.

2. Process of claim 1 wherein the catalyst is a secondary aliphatic amine.
3. Process of claim 2 wherein the catalyst is piperidine.
4. Process of claim 3 wherein the ester of malonic acid is dimethyl malonate.
5. Process of claim 3 wherein the ester of malonic acid is methyl allyl.
6. Process of claim 3 wherein the ester of malonic acid is methyl ethyl.
7. Process of claim 3 wherein the ester of malonic acid is methyl methoxy ethyl.
8. A compound having the formula

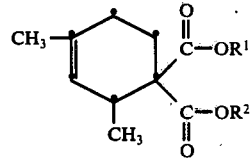

wherein $R^1$ is allyl and $R^2$ is methyl.

* * * * *